United States Patent [19]

Loftsson et al.

[11] Patent Number: 4,859,707
[45] Date of Patent: Aug. 22, 1989

[54] SULFUR-SUBSTITUTED PHENYLACETAMIDES

[75] Inventors: Thorsteinn Loftsson, Reykjavik, Iceland; Nicholas Bodor, Gainesville, Fla.

[73] Assignee: Key Pharmaceuticals, Inc., Miami, Fla.

[21] Appl. No.: 525,634

[22] Filed: Aug. 23, 1983

[51] Int. Cl.$^4$ .................. A61K 31/165; C07C 103/12
[52] U.S. Cl. .................................. 514/625; 514/821; 564/192
[58] Field of Search ............ 564/192; 424/324; 514/625, 821

[56] References Cited

U.S. PATENT DOCUMENTS

| | | | |
|---|---|---|---|
| 2,723,279 | 11/1953 | Hoepk et al. | 564/194 X |
| 3,161,680 | 12/1964 | McManus | 564/192 |
| 3,542,850 | 11/1970 | Jansen | 564/194 X |
| 3,770,824 | 11/1973 | Phillips | 564/215 |
| 4,327,111 | 4/1982 | Sundeen et al. | 564/192 |

Primary Examiner—Robert V. Hines
Attorney, Agent, or Firm—Anita W. Magatti; Stephen I. Miller

[57] ABSTRACT

This invention relates to sulfur-substituted phenylacetamides of the formula

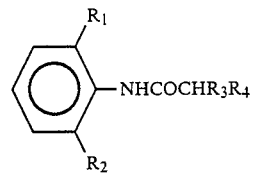

wherein $R_1$, $R_2$ and $R_3$ may be the same or different and are H or $CH_3$; $R_4$ is $SR_5$,

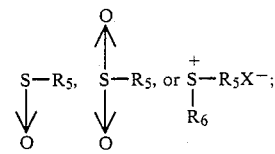

$R_5$ and $R_6$ may be the same or different and are lower alkyl containing 1–4 carbon atoms and $R_5$ and $R_6$ may be taken together with S to form a 5–7 member ring; and $X^-$ is a pharmaceutically acceptable anion, which exhibit arrhythmia activity.

9 Claims, No Drawings

SULFUR-SUBSTITUTED PHENYLACETAMIDES

The invention relates to novel sulfur-substituted phenylacetamides useful in the treatment of arrhythmia.

Arrhythmia has been defined as any variation from the normal rhythm of the heart beat. The cardiac impulse (heart beat) is normally initiated at the automatic, as pacemaker, cells of the S-A node by their spontaneous depolarization during diastole. Disorders of impulse generation include premature contractions (extra systoles) originating in abnormal or ectopic foci in atria or ventricles, paroxysmal supraventricular tachycarida, atrial flutter, atrial fibrillation and ventricular tachycardia and fibrillation. Ventricular arrhythmia can occur during cardiac surgery or result from myocardial infarction. Paroxysmal ventricular tachycardia presents a particular serious problem because the patient, if left untreated, will usually develop heart failure.

Lidocaine is considered one of the most useful drugs in the treatment of acute ventricular arrhythmia. Despite rapid and relatively complete absorption, oral administration of lidocaine is not clinically useful due to extensive first-pass metabolism and short half-life. Following intravenous administration, it is rapidly taken up by highly perfused organs, such as liver, which is considered the prime site of its metabolism, heart, brain, lungs, and kidney, leaving only about 15% of the dose in blood. In humans and most other species studied, the major pathway of lidocaine biotransformation appears to be N-dealkylation followed by secondary oxidation, conjugation, and hydrolysis. There is some indication that its metabolites may be responsible for the central nervous system toxicity observed when lidocaine is administered. Other arrhythmia drugs currently in use are also far from satisfactory, and the development of a long-acting, orally available arrhythmia agent exhibiting minimal side effects would fill an important need.

The present invention relates to a novel class of sulfurcontaining phenyl acetamides of the formula:

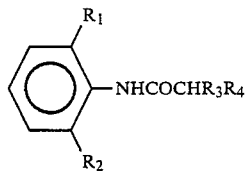

wherein $R_1$, $R_2$ and $R_3$ may be the same or different and are $R_4$ is $SR_5$,

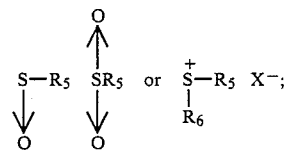

$R_5$ and $R_6$ may be the same or diffrent and are lower alkyl containing 1-4 carbons (methyl, ethyl, propyl, butyl and isomers thereof); $R_5$ and $R_6$ may be taken together with S to form a 5-7 member ring; and $X^-$ is a pharmaceutically acceptable anion. These compounds exhibit antiarrythmic activity and generally are less toxic than lidocaine.

The alkylthio compounds of the inventions are made by reacting an appropriately substituted aniline with an alkylthioacetyl halide

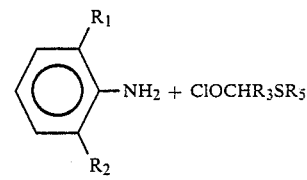

in an inert solvent and in the presence of a weak base such as a tertiary amine. These compounds are converted by oxidation under relatively milder conditions to the corresponding sulfinyl compounds ($R_4=SOR_5$) and by oxidation under stronger conditions to the corresponding sulfonyl compounds ($R_4=SO_2R_5$). Sulfonic salts are most conveniently prepared from the corresponding alkylthiophenylacetamides by reaction with a lower alkyl halide.

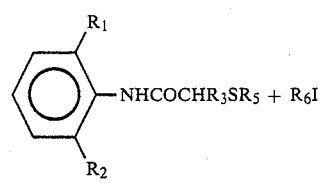

The resultnat halide salt may be converted to other pharmaceutical salts in the usual manner, for example, by exchange of a pharmaceutically acceptable anion for the halide, directly or via the hydroxide. Suitable pharmaceutically acceptable anions include, but are not limited to chloride, bromide, phosphate, sulfate, citrate, tartrate, benzoate, acetate, sulfate, etc.

The compounds of the invention exhibit arrhythimia activity in various test animals. 2-Dimethylsulfonic-N-(2,6-dimethylphenyl)acetamide iodide and 2-ethylthio-N-(2,6-dimethylphenyl)acetamide were particularly stable towards human plasma, esterase, and butyryl cholinesterase; no degradation could be observed over a period of 2-3 hours. The iodide was hydrolyzed very slowly by bovine liver microsomes and was absorbed slowly after oral administration to rats; significant amounts of the unchanged compound could be detected in the blood, about 7% in the feces and nothing in the urine. 2-Ethylthio-N-( 2,6-dimethylphenyl)acetamide also appeared to exhibit good bioavailability; no unchanged compound could be detected in the feces or the urine. Only minimal amounts of either compound could be detected in the urine after intravenous injection to rats. Both compounds showed considerable arrhythmia activity in dogs; somewhat larger doses were required to produce reversion to normal rhythm than that with lidocaine but the duration of the effect was much longer.

The compounds of the invention can be administered in a number of dosage forms. For example, in oral unit dosage forms such as tablets, capsules, pills, powders or granules or formulated into other pharmaceutically acceptable dosage forms by conventional methods known to the pharmaceutical art. These compounds can also be administered parenterally in a manner analogous to that used with lidocaine. An effective but non-toxic quantity of the compound is employed in treatment, generally 1-5mg/kg body weight. The exact dosage regimen is selected in accordance with a variety of factors including the type, age, weight, sex, and medical condition of the patient, the severity of the arrythmia and the particular compound employed.

Our invention is further illustrated by the following non-limiting examples:

EXAMPLE 1

2-Methylthio-N-(2,6-dimethylphenyl)acetamide.

To a chilled solution containing 1.21 g (10 mmols) of 2,6-dimethylaniline in 10 ml chloroform was added, in portions over 10 min with stirring, 1.25 g (10 mmols) of methylthioacetyl chloride. After 20 min, 0.79 g (10 mmols) of pyridine was added to the solution, and the temperature was allowed to elevate to room temperature under stirring for 25 min. The reaction mixture was washed once with 5% aqueous hydrochloric acid and twice with water. The organic layer was dried over anhydrous sodium sulfate and evaporated under reduced pressure to afford white crystalline compound, which was purified further by recrystallization from isopropyl alcohol (87% yield), mp 116°–117° C.

Anal.—Calc for $C_{11}H_{15}NOS$: C, 63.12; H, 7.22; N, 6.69; S, 15.32. Found: C, 63.19; H, 7.24; N, 6.69; S, 15.25.

EXAMPLE 2

2-Dimethylsulfonic-N-(2,6-dimethylphenyl)acetamide iodide.

To a stirred solution of 2.09 g (10 mmol) of 2-methylthio-N-(2,6-dimethyl)phenylacetamide in a mixed solvent of 20 ml acetonitrile and 30 ml diethyl ether was added 10 ml of methyl iodide. The reaction mixture was stirred at room temperature for 23 hr. The pale-yellow crystals formed were washed twice with diethyl ether and dried in vacuo (31% yield), mp 123°–124° C.

Anal.—Calc for $C_{12}H_{18}INOS$: C, 41.03; H, 5.17; N, 3.99; S 9.13. Found: C, 40.97; H, 5.21; N, 3.97; S. 9.09.

EXAMPLE 3

2-Methylsulfinyl-N-(2,6-dimethylphenyl)acetamide.

To a methylene chloride solution containing 2.09 g (10 mmol) of 2-methylthio-N-(2,6-dimethylphenyl)acetamide was added, in portions over 30 min with stirring at 5° C., 2.16 g (10 mmol) of m-chloroperbenzoic acid (80% solution). The reaction mixture was kept at 5° C. for an additional 1.25 hr. The precipitate formed was filtered and washed twice with methylene chloride. The filtrate and washings were combined, washed once with saturated aqueous sodium bicarbonate solution, dried over anhydrous sodium sulfate, and evaporated under reduced pressure. The residue was recrystallized from ethyl acetate to afford white crystalline compound (88% yield), mp 112°–114° C.

Anal.—Calc for $C_{11}H_{15}NO_2S$: C, 58.64; H, 6.70; N, 6.22; S, 14.23. Found: C, 58.65; H, 6.72; N, 6.19; S, 14.12.

EXAMPLE 4

2-Methylsulfonyl-N-(2,6-dimethylphenyl)acetamide.

Using the method described in Example 3 but with 2 equivalents of m-chloroperbenzoic acid, afforded the sulfonyl product (78% yield), mp 193°–196° C.

Anal.—Calc. for $C_{11}H_{15}NO_3S$: C, 54.75; H, 6.27; N, 5.80; S, 13.29. Found: C, 54,89; H, 6.32; N, 5.72; S, 13.21.

EXAMPLE 5

2-Ethylthio-N-(2,6-dimethylphenyl)acetamide.

To a chilled chloroform solution containing 12.1 g (0.1 mol) of 2,6-dimethylaniline was added, in portions over 20 min with stirring, 15.0 g (0.1 mol) of ethylthioacetyl chloride. After 10 min 8.50 g (0.1 mol) of pyridine was added to the solution and the temperature was allowed to elevate to room temperature under stirring for 2 hr. The reaction mixture was washed once with 3% aqueous hydrochloric acid and twice with water, dried over anhydrous sodium sulfate, and evaporated under reduced pressure. The residue was recrystallized from isopropyl alcohol and diethyl ether to afford crystalline compound (84% yield), mp 96°–98° C.

Anal.—Calc for $C_{12}H_{17}NOS$: C, 64.54; H, 7.67; N, 6.72; S, 14.63. Found: C, 64.45, H, 7.71; N, 6.26; S, 14.31.

EXAMPLE 6

2-Ethylsulfinyl-N-(2,6-dimethylphenyl)acetamide.

The method of Example 3 was repeated, starting with 2.23 g (10 mmol) of 2-ethylthio-N-(2,6-dimethylphenyl)acetamide. Recrystallization from ethyl acetate resulted in pure crystalline compound (83% yield), mp 114°–115° C.

Anal.—Calc for $C_{12}H_{17}NO_2S$: C, 60.22; H, 7.16; N, 5.85; S, 13.40. Found: C, 60.27; H, 7.16; N, 5.80; S, 13.36.

EXAMPLE 7

2-Ethylsulfonyl-N-(2,6-dimethylphenyl)acetamide.

Using the method of Example 4 (2 equivalents of m-chloroperbenzoic acid) 2-ethylthio-N-(2,6-dimethylphenyl)-acetamide was oxidized to the desired sulfonyl compound in an 75% yield, mp 128°–130° C.

Anal.—Calc. for $C_{12}H_{17}NO_3S$: C, 56.45; H, 6.71; N, 5.49; S, 12.56. Found: C, 56.48; H, 6.72; N, 5.44; S, 12.50

EXAMPLE 8

The biological test procedures, the results of which were noted previously, were carried out as follows:

A. Stability toward human plasma

The freshly collected human plasma was stored in a refrigerator and used within 1 week from the date it was collected. A portion of 50 ml at a standard methanol solution of the compound to be tested was mixed with 7.0 ml of plasma, previously equilibrated to 37.0° C., to result in an initial concentration of 0.2 mg/ml. Samples of 1.0 ml were withdrawn from the test medium, mixed immediately with 4.0 ml of ice cold 95% ethanol, and placed in a freezer. When all samples had been collected, they were centrifuged and the supernatant analyzed by HPLC.

B. Stability toward purified esterases

The effect of esterase (carboxylic-ester hydrolase, EC 3.1.1.1) and butyryl cholinesterase (EC 3.1.1.8), isolated from porcine liver and horse serum, was tested as follows: A portion of the enzyme and 30 ml of a standard solution of the compound in methanol were added to 2.50 ml of 0.05M TRIS buffer, pH 8.0, previously equilibrated to 37.0° C., resulting in solutions containing 5.2 units of enzyme and 0.4 mg of compound in one ml.

Aliquots (50 ml) were injected into the column at various intervals.

C. Metabolism in bovine liver microsomal preparations

Two kg of minced bovine liver were mixed with 4 liters of homogenization medium (0.34M sucrose, 1 mM EDTA, and 5 mM TRIS-HCI buffer ph 7.5) and sieved through a screen. The sieved tissue was homogenized for 2 min in a Tekmar grinder. The homogenate was centrifuged successively at 980 g for 10 min and 10960 g for 10 min. The resulting supernatant was then centrifuged at 31300 g for 45 min. All procedures were carried out at 4° C. The microsomal pallet was suspended in an equal volume of 20 mM TRIS-HCI buffer pH 8.0 containing 1 mM EDTA. Centrifugation of this suspension at 123000 g for 90 min gave a pallet which is referred to as the washed microsomes. This pallet could be stored frozen for months with little loss of activity.

The washed microsomes were mixed in a ratio of 1:2 (v/v) with 50 mM TRIS-HCI buffer ph 8.0. To 3.0 ml of this solution, previously equilibrated to 37.0° C., was added 0.2 ml of a standard solution of the compound to be tested resulting in an initial concentration of 1 mg/ml. Samples of 0.50 ml were withdrawn from the test medium, mixed immediately with 1.0 ml of ice cold 95% ethanol and place in a freezer. When all samples had been collected, they were centrifuged and the supernatant analyzed by HPLC.

D. In vivo evaluation in rats

A solution of test compound in DMSO was injected slowly through the jugular vein (65 mg/kg) to a group of female Wistar rats (150–200 g), 1.00 ml blood samples were taken at various time intervals, mixed with 2.00 ml of ice cold acetonitrile, and placed in a freezer. When all samples had been collected, they were centrifuged and the supernatant analyzed by HPLC. In a separate experiment urine samples were collected after i.v. administration of the test compound. A solution of test compound in polyethylene glycol was given p.o. to a group of rats (0.25 g/kg) and blood samples analyzed as before. Also, urine and feces samples were analyzed after p.o. administration of the test compound.

E. Estimation of $LD_{50}$ in mice

The $LD_{50}$ in white CD-1 male mice (average mass, 24.0±0.1 g) was estimated. A solution of the compound to be tested in dimethysulfoxide was injected intraperitoneally and the animals observed for 48 hr. The dose administered was gradually increased until about one-third of the animals in each group had died.

| Compound | No. of Mice | $LD_{50}$ mg/kg |
|---|---|---|
| lidocaine | 40 | 130 |
| Example 2 | 25 | 300 |
| Example 5 | 24 | 2100 |

F. Evaluation of antiarrhythmic activity in dogs

Dogs of either sex were anesthetized with pentabarbital sodium, 30 mg/kg, i.v. A lead II EKG was recorded and heart rate monitored on a Grass polygraph with appropriate signal treatment modules. A venous catheter was introduced into the inferior vena cava via a femoral vein. After a 20 minute stabilization period during which fast paper speed record segments (100 mm/sec) were taken to assess EKG profile, a 40 mg/kg dose of ouabain was injected intravenously as bolus. This was followed by 5 mg/kg doses of ouabain i.v., every 10 minutes, until a ventricular arrthymias occured—at lest 50% ventricular or septal ectopic beats. This usually occurred after a total dose of about 60 mg/kg. After 10 min of sustained arrhythmia, the compound to be tested was given by i.v. in fusion at a rate of 0.5 mg/kg/min (2 ml/min, flow-rate). The infusion was maintained until a normal sinus node heart rhythm was noted. The infusion was stopped and the total dose of compound administered was determined. The length of time that the normal sinus rhythm persisted after the end of infusion of the compound was also determined.

| Compound | No. of Dogs | Dose ± s.d. | Duration |
|---|---|---|---|
| lidocaine | 13 | 1.84 ± 0.32 | 1.23 ± 0.37 |
| Example | 2 | 3.82 ± 0.85 | 10,16, >15, >,20 |
| Example | 5 | 2.5 ± 2.8 | >20, >20 |

In the table above, "dose" is dose of compound mg/kg producing reversion to normal rhythm. "Duration" is duration in minutes of normal sinus rhythm after drug infusion.

We claim:

1. Compounds of the formula

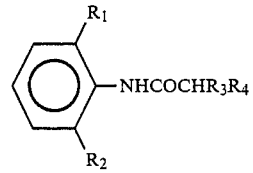

wherein $R_1$, $R_2$ and $R_3$ may be the same or different and are H or $CH_3$; $R_4$ is $SR_5$,

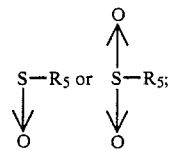

$R_5$ is lower alkyl containing 1–4 carbon atoms.

2. Compounds according to claim 1 wherein $R_4$ is $SR_5$.

3. The compound according to claim 2, 2-ethylthio-N-(2,6-dimethylphenyl)acetamide.

4. Compounds according to claim 1 wherein $R_4$ is

5. The compound according to claim 4, 2-methylsulfinyl-N-(2,6-dimethylphenyl) acetamide.

6. Compounds according to claim 1 wherein $R_4$ is

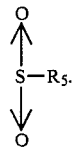

7. The compound according to claim 6, 1,2-ethylsulfonyl-N-(2,6-dimethylphenyl)acetamide.

8. A method for the treatment of arrhythmia which comprises administering to a patient having an arrhythmia heart beat an antiarrythmically effective amount of a compound of the formula

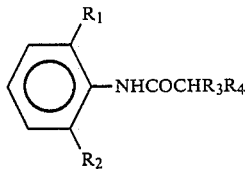

wherein $R_1$, $R_2$ and $R_3$ may be the same or different and are H or $CH_3$; $R_4$ is $SR_5$,

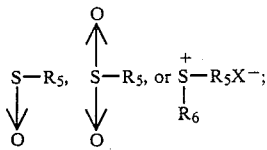

$R_5$ and $R_6$ may be the same or different and are lower alkyl containing 1–4 carbon atoms and $R_5$ and $R_6$ may be taken together with S to form a 5–7 member ring; and $X^-$ is a pharmaceutically acceptable anion.

9. A pharmaceutical anti-arrhythmia composition in dosage unit from comprising an antiarrythmically effective amount of a compound of the formula

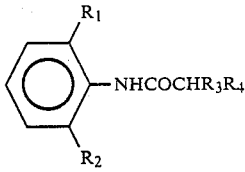

wherein $R_1$, $R_2$ and $R_3$ may be the same or different and are H or $CH_3$; $R_4$ is $SR_5$,

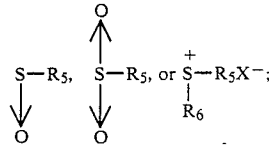

$R_5$ and $R_6$ may be the same or different and are lower alkyl containing 1–4 carbon atoms and $R_5$ and $R_6$ may be taken together with S to form a 5–7 member ring; and $X^-$ is a pharmaceutically acceptable anion.

* * * * *